(12) United States Patent
Sinclair et al.

(10) Patent No.: US 8,796,012 B2
(45) Date of Patent: Aug. 5, 2014

(54) GRATING-BASED EVANESCENT FIELD MOLECULAR SENSOR USING A THIN SILICON WAVEGUIDE LAYER

(75) Inventors: Bill Sinclair, Manotick (CA); Jens Schmid, Ottawa (CA); Philip Waldron, Ottawa (CA); Dan-Xia Xu, Ottawa (CA); Adam Densmore, Orleans (CA); Trevor Mischki, Ottawa (CA); Greg Lopinski, Ottawa (CA); Jean Lapointe, Ottawa (CA); Daniel Poitras, Ottawa (CA); Siegfried Janz, Ottawa (CA)

(73) Assignee: National Research Council of Canada, Ottawa (CA)

( * ) Notice: Subject to any disclaimer, the term of this patent is extended or adjusted under 35 U.S.C. 154(b) by 464 days.

(21) Appl. No.: 13/129,892

(22) PCT Filed: Dec. 2, 2009

(86) PCT No.: PCT/CA2009/001764
§ 371 (c)(1),
(2), (4) Date: May 18, 2011

(87) PCT Pub. No.: WO2010/063116
PCT Pub. Date: Jun. 10, 2010

(65) Prior Publication Data
US 2011/0223688 A1  Sep. 15, 2011

Related U.S. Application Data

(60) Provisional application No. 61/193,475, filed on Dec. 2, 2008.

(51) Int. Cl.
*C12M 1/34* (2006.01)
*G01N 33/543* (2006.01)
*G01N 33/551* (2006.01)

(52) U.S. Cl.
CPC ........ *G01N 33/54373* (2013.01); *G01N 33/551* (2013.01); *Y10S 435/808* (2013.01); *Y10S 436/805* (2013.01)
USPC ..................... 435/288.7; 422/82.11; 435/808; 436/164; 436/524; 436/527; 436/805

(58) Field of Classification Search
None
See application file for complete search history.

(56) References Cited

U.S. PATENT DOCUMENTS

| 4,815,843 | A * | 3/1989 | Tiefenthaler et al. ......... 356/128 |
| 7,008,794 | B2 | 3/2006 | Goh et al. |
| 7,315,679 | B2 | 1/2008 | Hochberg et al. |
| 7,368,281 | B2 | 5/2008 | Mozdy et al. |
| 7,778,499 | B2 | 8/2010 | Janz et al. |
| 2006/0008206 | A1 | 1/2006 | Maisenhoelder et al. |
| 2007/0237460 | A1 | 10/2007 | Fan et al. |
| 2010/0165351 | A1 | 7/2010 | Xu et al. |

OTHER PUBLICATIONS

Densmore et al., "A Silicon-on-Insulator Photonic Wire Based Evanescent Field Sensor", IEEE Photonics Technology Letters, vol. 18(23), p. 2520-2522, 2006.
Densmore et al., "Thin Silicon Waveguides for Biological and Chemical Sensing", Silicon Photonics II, Proc. of SPIE vol. 6477, p. 647718-1-647718-10, 2007.
Lukosz, W., "Priniciples and Sensitivities of Integrated Optical and Surface Plasmon Sensors for Direct Affinity Sensing and Immunosensing", Biosensors & Bioelectronics, vol. 6, p. 215-225, 1991.
Janz, S. et al., "Microphotonic Elements for Integration on the Silicon-on-Insulator Waveguide Platform", IEEE Journal of Selected Topics in Quantum Electronics, vol. 12(6), p. 1402-1415, 2006.

\* cited by examiner

*Primary Examiner* — Chris L Chin
(74) *Attorney, Agent, or Firm* — Catherine Lemay

(57) ABSTRACT

A technique for high sensitivity evanescent field molecular sensing employs a detection scheme that simultaneously couples a polarized beam to a single mode of a waveguide, and couples the polarized beam out of the waveguide to specularly reflect the beam by the same grating. Strong interaction with the single (preferably TM) mode is provided by using a silicon on insulator (SOI) wafer having a waveguide thickness chosen between 10-400 nm so that the majority of the mode field strength spans the evanescent field. Well known, robust techniques for producing a grating on the waveguide are provided. Interrogation from a backside of the SOI wafer is taught.

23 Claims, 5 Drawing Sheets

GRATING-BASED EVANESCENT FIELD MOLECULAR SENSOR USING A THIN SILICON WAVEGUIDE LAYER

CROSS-REFERENCE TO RELATED APPLICATIONS

This application is a national phase entry of International Patent Application PCT/CA2009/001764 filed Dec. 2, 2009, which claims the benefit of U. S. Provisional Patent Application Ser. No. 61/193,475 filed Dec. 2, 2008.

FIELD OF THE INVENTION

The present invention relates in general to evanescent field molecular sensors, and in particular to a molecular sensor having a waveguide providing an optical mode exhibiting a high evanescent field strength in a region of the waveguide functionalized with monolayer of receptors for a specific target molecule, the waveguide being formed of a robust, thin single-crystal silicon layer, upon which a grating of, for example, silicon dioxide is deposited and selectively etched, to produce superior sensitivity in comparison with prior art sensors.

BACKGROUND OF THE INVENTION

Molecular sensors that use evanescent field interactions to detect and quantify analytes have been known for nearly two decades. Applications for such sensors include chemical and biohazard sensing, food and water testing, and biological screening for medical applications. These sensors can also be applied in research and development in academic labs (proteomics, gene studies, etc.) and for testing in the pharmaceutical industry.

A recently issued U.S. Pat. No. 7,368,281 to Mozdy et al. teaches a grating-coupled waveguide sensor system including: an evanescent-field sensor having a substrate surface with at least a parital bio- or chemo-responsive layer that forms a part of a serially renewable sensing region; an optical interrogation apparatus for monitoring the bio- or chemo-responsive layer; and an air-fluid delivery system. The substrate has reactant and non-reactant regions and can be modified with one or more materials to enhance immobilization of the bio- or chemo-responsive layer.

According to the teachings of Mozdy et al. the sensor system preferably includes a substrate with tensile strength and pliability that can be supplied from a dispensing device as a single unit in a continuous fashion; and the substrate is configurable to a fraction of its fully extended length along its longest dimension without breaking, and can be retrieved from such configuration as a continuous body suitable for performing molecular interactive assays with toxin targets. For instance, the substrate is an optically transparent (polymer) film of about 50 µm to about 2 mm thick. Alternatively, the evanescent-field sensor has a substrate in the form of a revolving platform.

Mozdy et al. in FIG. 9 graph the relationship between angle and wavelength for a particular commercial sensor. The different curves show behavior for both TE and TM polarizations for two different cover indices (water index=1.333). There is a slightly wider spread between TM modes than TE modes.

Low loss single-mode waveguides in the form of thin Silicon on insulator (SOI) substrates have been demonstrated, for example, in U.S. Pat. No. 7,315,679 to Hochberg et al. Hochberg et al. teach a system for influencing a waveguide using thin silicon structures having electrodes coupled thereto. Hochberg et al. note that it is known to provide waveguides having, a patterned silicon pathway formed on a silicon dioxide layer that is formed over a substrate. Light is substantially guided within the patterned silicon pathway. Advantageously, these waveguides can be substantially thin (e.g. from 100-200 nm, such as 120 nm). Hochberg et al. teach that the thin geometry is helpful in obtaining high field concentrations in the waveguide cladding, and that intense field concentrations in the cladding may be useful, for example, in the construction of sensors where interactions of the cladding with external stimulus perturb the propagation of light in the waveguide. The stimulus can thereby be sensed by monitoring the optical output of the waveguide. There are a wide number of sensor designs possible to leverage this principle.

In previously filed U.S. Ser. No. 11/898,660, Applicant has shown that photonic wire evanescent field (PWEF) sensors have extremely high sensitivity to molecular binding and can be made small enough that arraying many sensors on a single chip is possible.

In previously filed WO 2008/141417, Applicant teaches a thin silicon SOI sensor in which a light beam travelling in the silicon waveguide creates an evanescent optical field on the surface of the sensing element adjacent to the boundary between the sensing element and the aqueous medium. Molecular interactions occurring on this surface affect the intensity or the phase of the light beam travelling through the waveguide by changing the effective refractive index of the medium. By measuring the effect on the intensity, phase, or speed of the light beam, the molecular interactions can be detected and monitored in real time. Various configurations in which the sensor can be used, such as in a ring resonator or a Mach-Zehnder interferometer are also illustrated. In all cases the light is inserted into the waveguide at the ends of the SOI sensor.

It is also known in the art to provide diffraction based detection of analytes, for example, as taught in U.S. Pat. No. 7,008,794 to Goh. Goh teaches determining analyte presence by the presence or absence of diffraction provided by a buildup of analyte on patterned functionalization.

Other references that may be relevant include: US2006/0008206: Waveguide plate and process for its production and microtitre plate, and US20070237460: Hollow Core Optical Ring Resonator Sensor, Sensing Methods, and Methods of Fabrication.

Thin dielectric waveguides have been studied and characterized by various research programs and the intensities of evanescent fields, and the effects of propagation on cladding index, have been studied.

There remains a need for improved sensitivity and ease of interrogation of molecular sensors, especially for molecular sensors that are produced using fabrication methods that are cost efficient and compatible with mass production. Silicon photonic wire PWEF sensors have high sensitivity, and offer many possibilities for the design of extremely compact integrated optical sensor circuits that can incorporate multiple sensor arrays and correct for sensor drift due to temperature fluctuations and other variables. However initial market acceptance of PWEF sensors may be constrained by the fact that it is a very different technology than the existing label free optical sensing tools such as surface plasmon resonance (SPR). While the integrated optical fabrication and packaging technologies required to implement PWEF sensors are well established in the telecommunications industry, these technologies are unfamiliar to users and equipment manufacturers in the molecular biology, pharmaceutical and food safety sectors. Furthermore, the nature of the semiconductor manufacturing process is such that fabrication and packaging of large quantities of silicon PWEF devices can be cost effective, but initial start-up costs may still represent a barrier when a large market has not yet been established.

Therefore there is a need for a silicon biosensor chip that retains some of the advantages of silicon PWEF sensors, such as high sensitivity, but has minimal fabrication and packaging requirements, and can be interrogated using low cost off the shelf optical components in similar arrangements to those found in established technologies. The grating based sensor described here fills this need, and by design can be incorporated in existing SPR measurements systems with only minor design modifications to the SPR optical read-out system.

SUMMARY OF THE INVENTION

Applicant has developed a molecular sensor with a silicon on insulator (SOI) wafer that exhibits improved sensitivity.

According to an aspect of the invention a molecular sensor is provided, comprising: a silicon on insulator (SOI) wafer including a single crystal silicon layer waveguide over a $SiO_2$ insulator layer, the waveguide having a diffraction grating on a sensor surface which is functionalized with receptors for a specific target molecule; such that the grating couples a polarized beam of light incident on the sensor surface to preferentially excite a single mode in the waveguide and equally to couple the single mode out to produce a sensed output; and the waveguide has a thickness of 10-400 nm, so that the single mode has an evanescent field strength at the surface of the waveguide that is comparable to or higher than the field strength at any point within the waveguide.

According to another aspect of the invention, a method of sensing a target molecule, if present, within a fluid flow, is provided comprising:

providing a silicon on insulator (SOI) wafer including a single crystal silicon layer waveguide over a $SiO_2$ insulator layer, the waveguide having a diffraction grating on a sensor surface that is functionalized with receptors for a specific target molecule;

applying the fluid flow to the sensor surface so that if the target molecule is present, it will preferentially attach to the receptors;

applying a polarized beam of light incident the sensor surface so that the diffraction grating couples the beam to preferentially excite a single mode in the waveguide and equally to couple the single mode out to produce a sensed output, the waveguide having a thickness of 10-400 nm, selected so that the single mode has an evanescent field strength at the surface of the waveguide that is comparable to or higher than the field strength at any point within the waveguide; and determining a property of the sensed output surface that varies with interaction of the evanescent field with the target molecules if present.

Applicant has found that the sensor response using a planar SOI waveguide with grating coupling of the beam to the waveguide produces similar sensitivity measurements to that of the silicon photonic wire sensor, such as the one described in our pending U.S. application Ser. No. 11/898,660. This represents a significant improvement in the art.

The SOI wafer has a single crystal silicon layer waveguide over a $SiO_2$ insulator layer. The waveguide has a top sensor surface on which a grating is provided. A sensor surface is functionalized with receptors for a specific target molecule. The grating is chosen so that that a polarized beam of light incident the sensor surface is preferentially coupled with a single mode of the waveguide and equally to couple the single mode out to produce a sensed signal, and the waveguide has a thickness of 10-400 nm so that the single mode has a peak evanescent field that is comparable to or larger than the field inside the waveguide, and is strongly localized near the surface of the waveguide. The single mode is preferably a TM mode, and the incident beam is preferably P-polarized. Interrogation of the sensor may be accomplished by measuring intensity of the reflected beam at a fixed wavelength and incident angle, measuring the wavelength spectrum, or measuring the reflected intensity change as incident angle is varied.

The grating may be formed of a 1 to 2000 nm thick dielectric layer having a regular spacing for effective coupling of the beam to the waveguide. The grating may be selectively etched from the silicon surface, or produced in other ways known in the art, however applicant prefers two other methods: the deposition of a layer having a different composition (such as a transparent polymer or an inorganic compound, more preferably silicon dioxide or silicon nitride), followed by selective etching to completely remove sections of the layer (e.g. using e-beam or stepper lithography); or patterning the functionalization of the top sensor surface, by selective deposition of the receptors directly on the silicon waveguide surface, such at taught by U.S. Pat. No. 7,008,794 to Goh et al. (the contents of which are incorporated herein by reference).

Preferably, the thickness of the waveguide is chosen to provide the single mode that has a region of highest field strength within a distance from the sensor surface that corresponds to where a monolayer of the target molecules would be located. If the functionalization layer is directly applied to the sensor surface that is substantially smooth, or if the functionalization is applied to the silicon top surface between the diffraction grating ridges, this distance would start from a negligible fraction of 1 nm to about 10 nm from the silicon top surface, and extend a mean length of the target molecules. If the functionalization is provided only on the ridge tops of the ridges of the grating, the distance will be further offset by the thickness of the grating. It will be noted that the field strength of the mode within the waveguide, including the evanescent field (outside of the waveguide/cladding) varies as a function of distance from the edge of the waveguide. Accordingly, an equivalent statement of the highest field strength requirement is that there is a distance d within the expected monolayer thickness over which the integral of the field strength is comparable to or higher than it is over any other continuous region of equal length.

Advantageously the incident beam may be applied from a bottom silicon layer of the SOI wafer so that the beam is not scattered, attenuated, refracted, or perturbed by transit through the sample fluid or fluid channels. Accordingly the bottom layer of the SOI may be coated with an antireflection film, to reduce reflection loss and eliminate interference fringes in the optical Fabry-Perot cavity formed by the substrate wafer.

The molecular sensor may further comprise a detector for measuring at least one of a phase and a power of the beam after transmission through, or reflection from, the sensor surface. In accordance with an alternative measurement setup, as taught by U.S. Pat. No. 7,008,794 to Goh, a diffracted image or pattern can be produced in dependence on the thickness and index of the grating that is built up to form the diffraction grating. Specifically the present invention can employ the diffraction grating and/or the diffraction imaging technique taught by Goh.

Applicant has also developed a method of sensing a target molecule, if present, within a fluid flow by providing a silicon on insulator (SOI) wafer consisting of a single crystal silicon layer waveguide over a SiO$_2$ insulator layer, the waveguide having a diffraction grating on a top sensor surface that is functionalized with receptors for a specific target molecule; applying the fluid flow to the sensor surface so that if the target molecule is present, it will preferentially attach to the receptors; applying a polarized beam of light incident the sensor surface so that the diffraction grating couples the beam to preferentially excite a single mode in the waveguide and equally to couple the single mode out to produce a sensed signal; and the waveguide has a thickness of 10-400 nm, so that the single mode has a higher evanescent field strength than the field strength within the waveguide; and determining property of light reflected from or transmitted through the sensor surface that varies with interaction of the evanescent field with the target molecules if present.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

A technique for high sensitivity molecular sensing is provided that uses evanescent field sensing using a simply constructed, high quality, molecular sensor. The technique involves simultaneously coupling a polarized beam to a single mode of a waveguide, and coupling the polarized beam out of the waveguide along the specular reflected beam direction by the same grating. This kind of field sensor eliminates the need for fibre coupling or more elaborate interference setups. The invention may be seen as the combination of the use of high quality, robust, simple Si fabrication technologies to produce a high sensitivity molecular sensor consisting of a single crystal Si waveguide with an efficiently deposited grating, to produce a sensor suited for detection with an efficient sensing technique that involves reflection or transmission for simplified optical detection.

Figure 1:
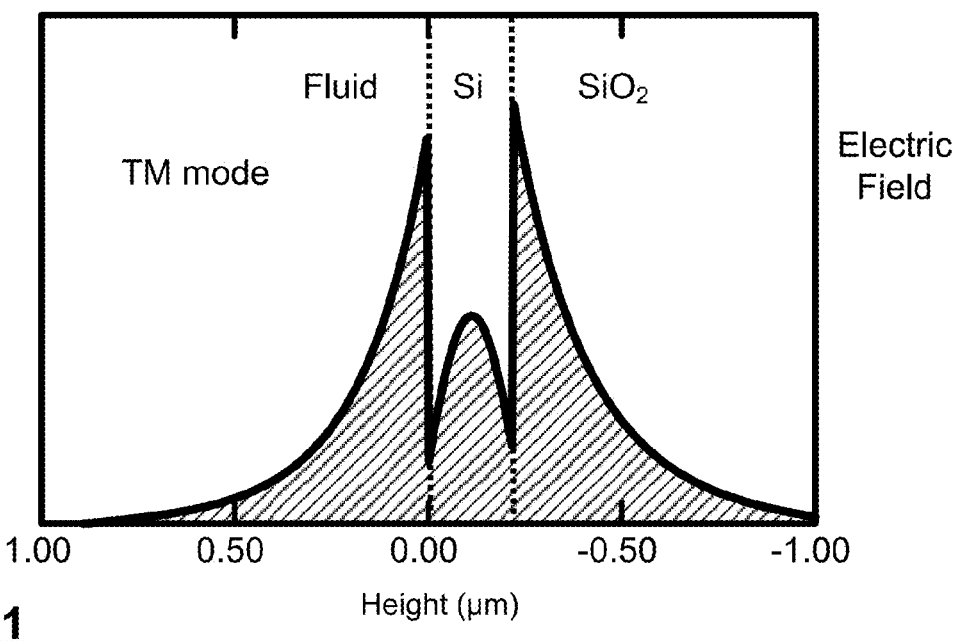
FIG. 1 is a schematic illustration of a waveguide mode field profile in a 220 nm thick silicon on insulator waveguide at a wavelength of λ=1550 nm mode field profile, exhibiting strong field strength in cladding.

An optimal silicon waveguide thickness for transverse magnetic (TM) polarized modes of wavelengths near 1550 nm, is ~220 nm. This gives a sensitivity to molecular binding that is higher than that of other commonly available waveguide platforms or surface plasmon resonance (SPR) methods [1]. FIG. 1 is a schematic illustration of a waveguide mode field profile in a 220 nm thick silicon on insulator waveguide at a wavelength of λ=1550 nm, exhibiting strong field strength in cladding. In fact, the single mode has an evanescent field strength at the sensor surface (0.00-0.006 µm) of the waveguide that is more than twice the maximum field strength within the waveguide. This waveguide mode field profile is based on the fluid consisting of water, but other fluids could alternatively be used.

Figure 1A:
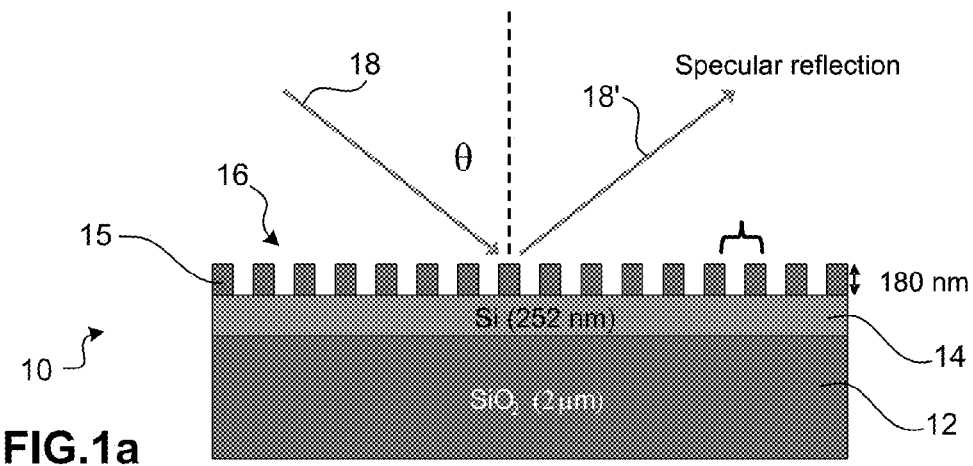
FIGS. 1a,b are schematic illustrations of a molecular sensor with a front side illumination scheme in accordance with an embodiment of the invention, in cross-section and perspective views, respectively.

FIGS. 1a,b schematically illustrate a molecular sensor 10 in accordance with a first embodiment of the invention, prior to functionalization. The sensor is formed from a silicon on insulator (SOI) platform consisting of an underlying silicon substrate (not shown in FIG. 1a), an insulator layer 12 composed of SiO$_2$, covered with a thin Si evanescent field waveguide 14. The top side of the waveguide 14 is a sensor surface 16 onto which a diffraction grating 15 has been patterned.

FIG. 1a additionally shows specific dimensions of a particular molecular sensor created and used to test the present invention. FIG. 1a also shows a wavevector of an incident polarized beam 18 of light directed onto the sensor surface 16. The diffraction grating 15 has of a spacing chosen for efficient coupling of the polarized beam 18 into the waveguide 14, and selectively excites a single mode within the waveguide 14 referred to herein as the interaction signal. In the present examples the interaction signal is in a Transverse Magnetic (TM) mode. The interaction signal is equally disposed to couple out of the waveguide 14 as the incident polarized beam is to enter the waveguide 14, because of the diffraction grating 15. The interaction signal that is coupled out from the waveguide 14 generates a sensed output signal. Depending on the effective index of refraction of the single mode (which depends on the index of refraction in the neighbourhood of the sensor surface in proportion to the field strength in that region), the sensed output is effectively phase shifted with respect to the compound specular reflection (i.e. the fixed weighted superposition of specular reflections from all of the interfaces that provide a static signal that interferes with the sensed output signal when the sensor is used in specular mode), by virtue of the change in matching of the grating with the waveguide mode. The sensor therefore emits the compound specular reflection, and sensed output in a direction of specular reflection 18'.

Figure 1B:
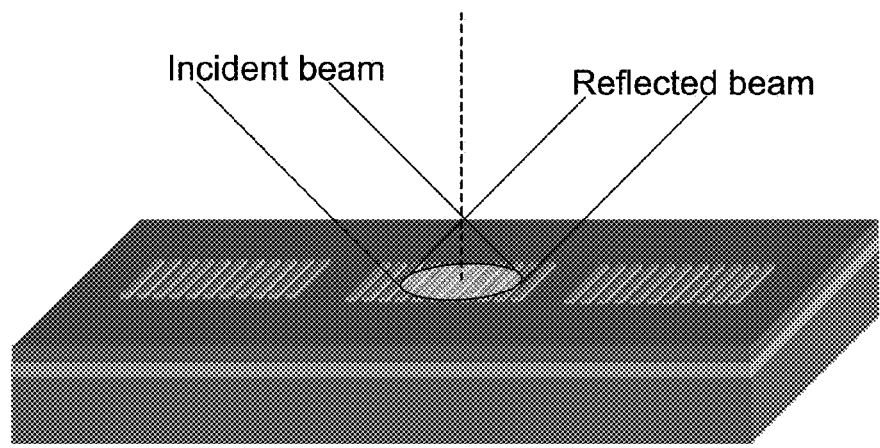

FIG. 1b also shows a supporting substrate also made of Si that is orders of magnitude thicker than the insulator layer 12.

The silicon waveguide sensor can be used at wavelengths from 1200 to 4000 nm, more preferably 1200-2000 nm, or more specifically from about 1280-1600 nm, or 1280-1350 and/or 1480-1600 nm for which cost-effective telecommunications laser and detection systems may be readily be deployed. For wavelengths near 1550 nm and using the TM polarized waveguide mode, an optimal silicon waveguide thickness near 220 nm gives a sensitivity to molecular binding that is, in theory, substantially higher than that for other commonly available waveguide platforms or surface plasmon resonance (SPR) methods [2]. The optimal waveguide thicknesses for other wavelengths can equally be computed by the method disclosed therein, using well known algorithms for calculating waveguide modes. Commercial mode solvers based on these algorithms are readily available.

The thin Si evanescent field waveguide 14 is of a carefully chosen thickness and composition. The composition is a single crystal Si material, as known in the art of semiconductor fabrication. While the waveguide 14 has an excellent uniformity of thickness and composition, it can be relatively inexpensively mass produced. While in general most waveguides provide a field amplitude that is largest within the waveguide (as is desirable to minimize waveguide losses and cladding thickness), and the evanescent field is relatively weak, it is possible to produce thin waveguides in which a highest field amplitudes are outside of the waveguide. In general this requires the use of a thin, high refractive index, core layer, and low index clading layers, and the guided light polarized perpendicular to the sensing surface (usually the TM waveguide mode). For example, for SOI structures as shown above, a thickness less than 400 nm results in a higher evanescent field than bulk field for 1550 nm light.

While continuously thinner waveguides provide increasing evanescent field strength relative to the field strength inside the waveguide, the penetration distance of the evanescent field also increases. As a result, to achieve the highest field strength within the neighbourhood of the sensor surface 16, a trade-off is called for.

By choosing the SOI structure and controlling the waveguide thickness, molecular sensors with high response to molecular bonding, are provided. Furthermore the $SiO_2$ surface chemistry of the sensor surface is advantageous in that it is a well known and characterized material with robust, repeatable binding options for functionalization.

In the examples Applicant has produced, the grating is formed by etching the grating lines into a very thin 180 nm $SiO_2$ layer deposited over the 220 nm thick Si waveguide layer, however this can alternatively be performed in many other ways. The grating period is chosen such that a beam of light incident at an angle theta of a wavelength lambda is coupled into the Si waveguide, and then coupled back out at the same angle as the specular beam reflected from the various layer surfaces.

The spatial period or pitch of the grating lines $\Lambda_g$ is chosen to match a resonant condition occurring when the grating period, effective index $N_{eff}$, incident angle $\theta$ and wavelength $\lambda$ all satisfy Eq. (1) for coupling the incident and reflected beam with the single mode, which is preferably the TM mode, in a manner well known in the art. In Eq. (1) the number m is an integer describing the diffraction order of the grating.

$$N_{eff} = \sin\theta + m\frac{\lambda}{\Lambda_g} \quad (1)$$

There are several parameters that can be chosen simultaneously to achieve a desired grating, such as the thickness of the grating, the surface area of the grating (covered by the beam), as well as the duty cycle of the grating, and these too are affected by a diameter of the beam, angles of incidence of the beam and numerous other factors in a manner well known in the art. Solutions to optimize such systems are computed by solvers known in the art.

In general, the thicker the diffraction grating 15 and the greater the refractive index difference between the diffraction grating 15 and the fluid, the more effective the coupling of the light from the beam into the waveguide, and the more effective the coupling of the light from the interaction signal into the sensed output. In general, the more effectively the incident beam excites of the single mode in the waveguide, the shorter the propagation distance of the light within the waveguide, before it is coupled out of the waveguide as the sensed output. The longer the beam propagates along the waveguide, and the higher the local change in index of refraction with the bonding or attachment of target molecules within the evanescent field, the stronger the effect of the binding within the evanescent field on the sensed output, and the stronger the sensed output signal is. Thus the thinner the grating, or the closer the index of the grating matches the fluid, the weaker the coupling, which, to a point, improves the sensitivity of the sensor output.

The strength of the sensed output signal also depends on the size of the grating and the surface area over which the grating is illuminated. For a given thickness and period of the diffraction grating 15, optimal grating size and illumination area can be calculated using numerical methods such as rigorous coupled wave analysis (RCWA), that are well known in the art for calculating the optical properties of gratings.

A final trade-off is in the line to space ratio, or duty cycle, of the grating. Typical diffraction gratings have spacings equal to ½ the pitch. It will be appreciated that in certain embodiments the functionalized surface area of the grating openings (i.e. the empty spaces between the lines of the grating) are most sensitive to the binding of the molecules. Accordingly, increasing the spacings relative to the pitch is expected to increase the TM mode's dependence on the molecule's presence (sensitivity), but at the expense of the efficiency of the coupling of the incident beam into the waveguide.

These sensors may be functionalized by coating the whole grating and sensor surface 16 with receptor molecules (such as biotin used in the example below) but by far the largest change in the index of refraction is produced by binding of target molecules in the valleys between the ridges (i.e. lines) of the grating.

Alternatively, the grating lines can be produced by patterned deposition of the receptor onto the waveguide, as taught by U.S. Pat. No. 7,008,794 Goh et al., the contents of which are incorporated herein by reference. In some embodiments, according to the teachings of Goh et al., the grating diffraction powers are very weak for no molecular binding, but grow linearly as target molecules bind to the functionalized grating pattern.

A total intensity of the sensed output varies with the phase of the interaction signal relative to the light specularly reflected from the planar interfaces in the waveguide structure. As the field strength is high in the neighbourhood of the sensor surface, for suitable coupling strengths into and out of the waveguide, the sensed output is very sensitive to the effective index of the silicon waveguide, and can be used to monitor molecular binding to the waveguide grating surface.

Advantageously, the optical layout for testing flow across the molecular sensor 10 is almost identical to that used in widely deployed surface plasmon resonance (SPR) systems, and can be implemented with relatively simple bulk optics, with little training.

Also advantageously, manufacturing of these molecular sensors is essentially a one step wafer scale process involving applying the grating on an SOI wafer, and no-chip level packaging is required. Functionalization can be performed in a manner well known in the art. If a 1 cm chip size is assumed, a six inch wafer should yield approximately 150 sensor chips, and each chip may contain from four 5 $mm^2$ gratings, up to 100 or more smaller sensor gratings depending, on specific sensor design and requirements.

The polarized beam is preferably a P-polarized beam. While the beam shown in FIG. 1b and wavevector 18 shown in FIG. 1a are directed from a front side, it is considered preferable in some embodiments to perform detection from the back side as described below, to avoid signal artefact that may be produced while passing through a sample fluid tested (and associated microfluidics), a monolayer of the target molecule (to the extent present), and the functionalization layer.

The SOI structure of the embodiments of FIGS. 2-5 is the same as that of the embodiment of FIGS. 1a,b, and accordingly descriptions of the corresponding components are not repeated here.

FIGS. 2-5 schematically illustrate molecular sensors interrogated from a back side. Accordingly it is preferred to coat a bottom silicon substrate of the SOI with an anti-reflection coating. This coating reduces reflection of the incident p-polarized beam of light, which may be a swept source or tunable laser beam, or a narrowband wavelength laser beam.

The anti-reflection coating also reduces internal reflection of the specular and diffracted beams from the back surface of the sensor chip, as well as multiple reflections of beams between various layer interfaces in the SOI wafer and the back surface of the sensor chip. In this way Fabry-Perot intensity fringes in the output signal are minimized.

FIGS. 2-5 also show a fluid flow, which may preferably be a liquid flow, over the sensor surface. It will be appreciated that macro, micro or nano fluidics could be used to control fluid motion over the sensor surface in myriad of ways. The flow could be within a channel, weir, dam or other still fluid body, as long as a desired interaction between the target molecules is provided.

Figure 2:
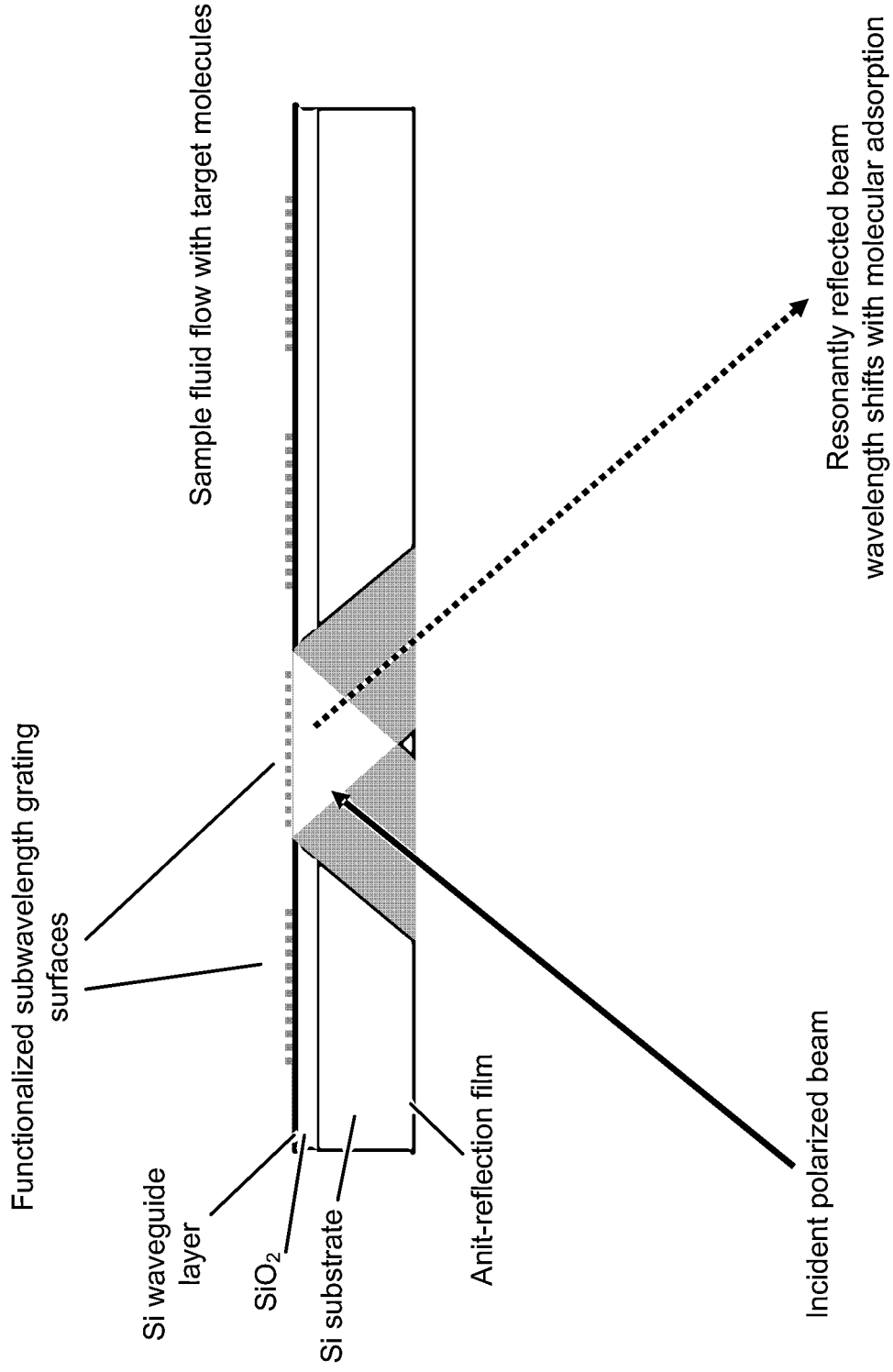
FIG. 2 is a schematic illustration of a molecular sensor with a back side illumination using specular detection, in accordance with an embodiment of the invention.

FIG. 2 schematically illustrates backside illumination with a specular reflection detection scheme. Reflected power is used to determine an efficiency of the coupling of the beam to the waveguide.

As taught in U.S. Pat. No. 7,008,794 Goh et al., higher (than 0) order diffracted beams can be used to detect evanescent field changes. The principle difference between the diffraction based detection, and specular reflection detection is that the transduction signal is the intensity of a higher order (i.e. m≠0, where the m=0 order diffraction corresponds to the specularly reflected beam direction) diffracted beam. This is shown in FIG. 3 for the same reflection geometry as before, and in FIG. 4 for the transmission geometry.

Figure 3:
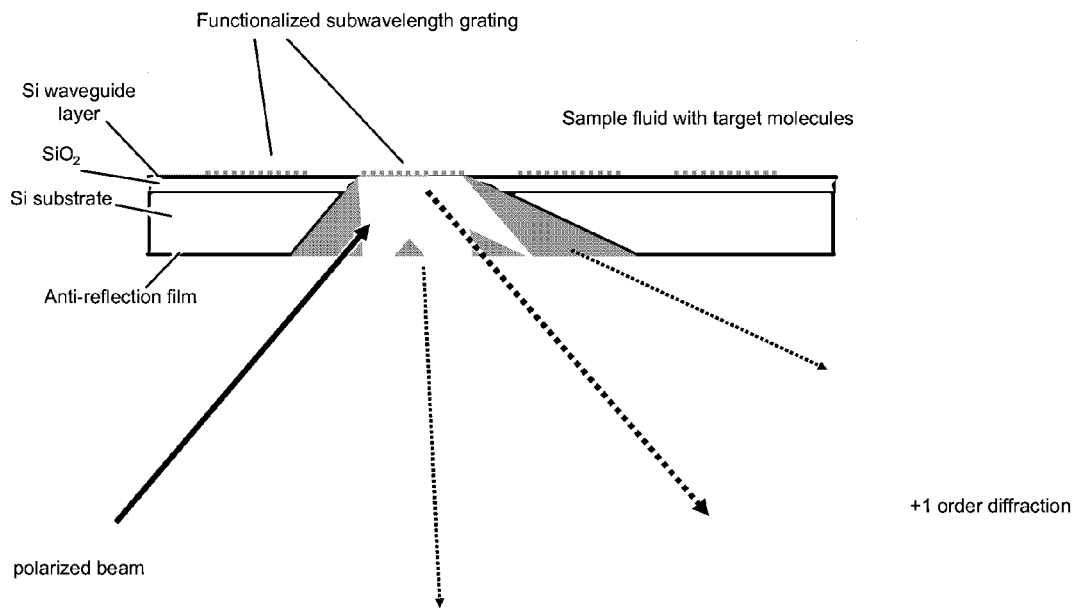
FIG. 3 is a schematic illustration of a molecular sensor with a back side illumination using reflected diffraction detection, in accordance with an embodiment of the invention.

As shown in FIG. 3, the waveguide grating sensor can be probed by monitoring the diffracted beam power. The m=+1 and m=−1 diffracted beams are shown along with the reflected beam ($0^{th}$ order diffraction). The power or angle of diffracted beams can be used to detect a concentration of the molecules, depending on the equipment available, etc.

Figure 4:
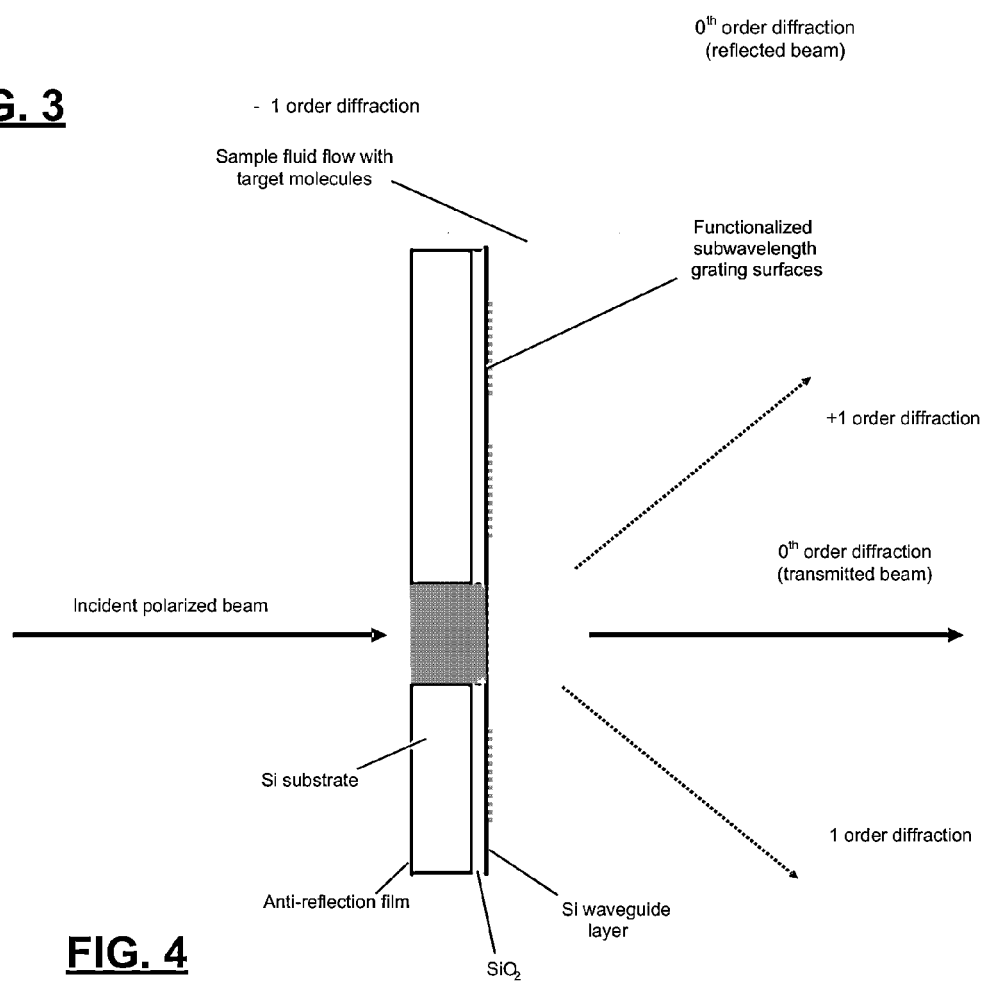
FIG. 4 is a schematic illustration of a molecular sensor with a back side illumination using transmitted diffraction detection, in accordance with an embodiment of the invention.

As shown in FIG. 4, the waveguide grating sensor can equally be probed in transmission detection by monitoring the power in a diffracted or transmitted beam. The m=+1 and m=−1 diffracted beams are shown here along with the transmitted beam ($0^{th}$ order diffraction).

Figure 5:
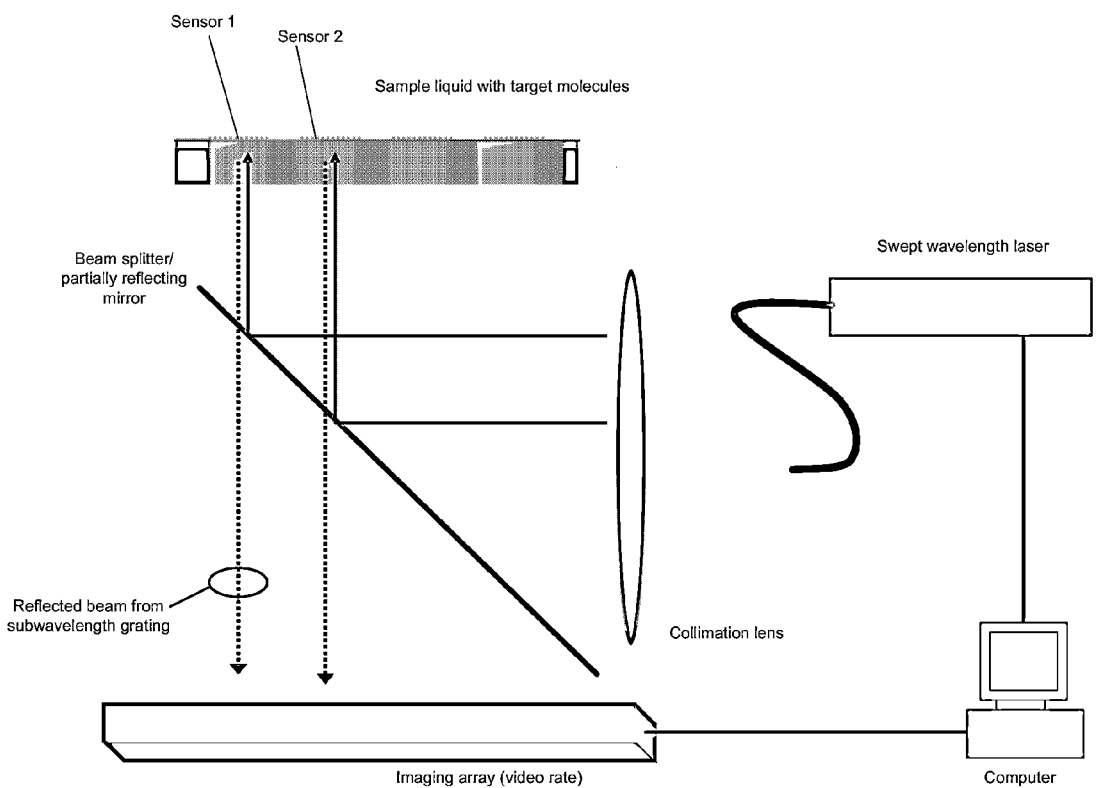
FIG. 5 is a schematic illustration of a multiplexed molecular sensor array with a back side illumination using specular detection, in accordance with an embodiment of the invention.

FIG. 5 is a schematic illustration of one possible optical layout for interrogating an array of grating mirror sensors using a swept wavelength laser synchronized with an imaging array. In this embodiment the light beam is incident at normal incidence through the silicon substrate so that microfluidics and liquid are not in the optical path.

The multiplexed sensor array can be made by using a SOI slab waveguide with several sensors formed by isolated gratings. The isolated gratings may be functionalized differently for attracting different targets, or may be the same to produce region-specific detection of the target molecule, for example. Efficiently, the entire array area surface may be illuminated by a collimated laser light from a swept wavelength laser source.

An imaging array is used to monitor the reflected beams from each sensor area. By synchronizing the image acquisition with the repeating wavelength scan of the swept wavelength source, one can simultaneously monitor the resonance wavelength from each sensor element, and thus monitor molecular binding simultaneously for many sensors. The number of sensors that can be monitored is primarily limited by the speed of the acquisition electronics, the swept wavelength source scan rate, and data-processing speed of the computer.

EXAMPLES

We have now done the following experiments that demonstrate that this sensor configuration works as stated, for both front side and backside illumination.

Numerical Modelling

Figure 6:
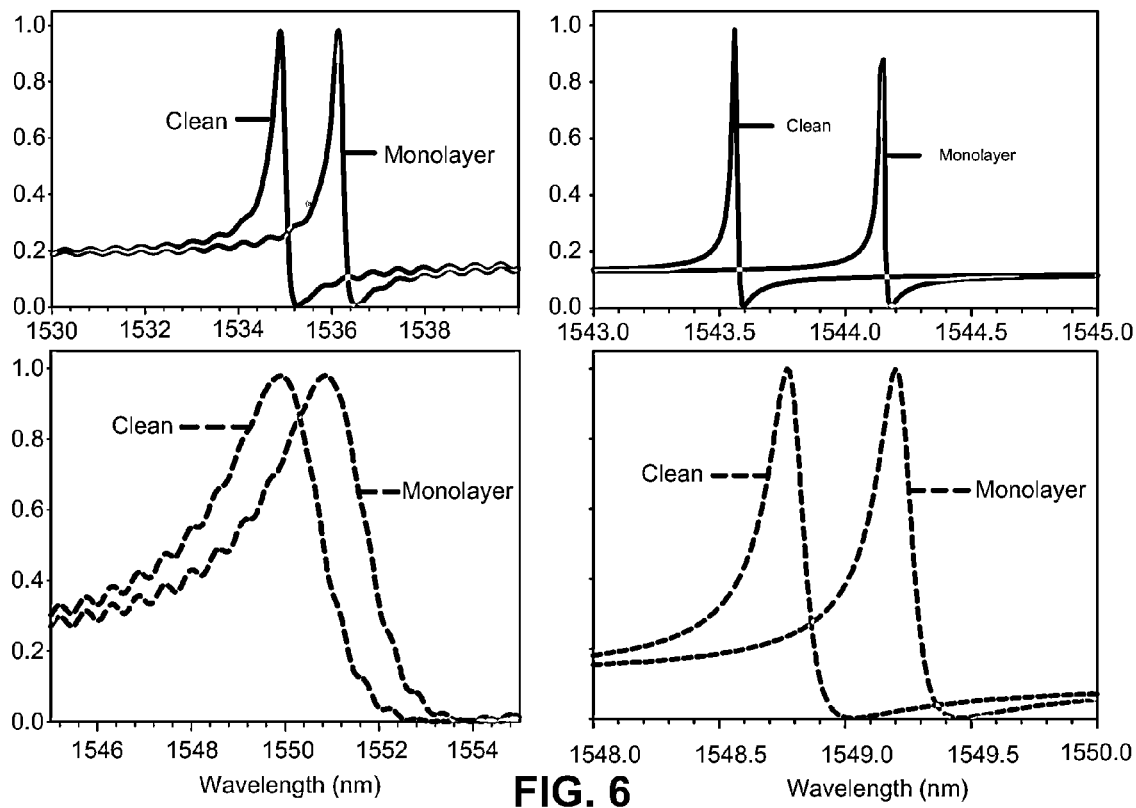
FIG. 6 is a graph of computed specular reflected power as a function of wavelength for different evanescent field interactions.

FIG. 6 shows the calculated resonances using rigorous coupled wave analysis (RCWA) before and after deposition of a streptavidin monolayer with air (left panels) and water (right panels) as the sensor medium. The simulation parameters includes the following: a $SiO_2$ grating having a duty cycle of 50%, a grating period of approximately 1.2 micrometers, and a grating layer thickness of either 50 nm (top panels) or 180 nm (bottom panels); the beam angle is 45°. The refractive index of the assumed streptavidin monolayer was n=1.5, and its thickness was 2 nm.

The spectra were calculated using the for the nominal sensor design parameters given below, for a clean surface and the streptavidin monolayer. These molecular film parameters are consistent with prior photonic wire sensor and ellipsometry measurements of streptavidin monolayers [2,3]. The spectra in FIG. 6 reproduces the measured line shapes and streptavidin-induced spectral shift very well. The differences in measured and calculated resonance wavelength, and resonance line shapes arise from deviations of the waveguide and grating structures from the nominal values used in the simulation, and the presence of some optical loss in the fabricated device.

It will be noted that the further apart the clean and monolayer peaks, and the narrower the bandwidth, the more easily distinguished a smaller change in concentration of the analyte. Accordingly the top right panel (water medium, 50 nm grating) provides the finest graded sensor, and the bottom left panel (air medium, 180 nm grating) provides the coarsest graded sensor. In fact, the top right panel represents an ideal sensor that is at least two orders of magnitude more sensitive than optimal SPR techniques.

Prototype

The binding of streptavidin protein molecules to biotin is used as an exemplary system to demonstrate this invention. The sensor was fabricated on a silicon on insulator wafer with a 220 nm top silicon layer (the waveguide), a 2 μm thick buried oxide ($SiO_2$) layer, and a 600 μm substrate wafer. The back of the wafer was polished, and a multilayer anti-reflection (AR) film was applied to eliminate unwanted reflections from the back surface.

A layer of hydrogen silsesquioxane (HSQ) photoresist was applied to a top sensor surface of the silicon waveguide by spin coating, and 7 mm×5 mm grating patterns were written by e-beam lithography and developed to produce a grating of 180 nm thick $SiO_2$ lines with a 1.2 μm pitch. This grating period was chosen to satisfy the resonant condition for coupling the incident and reflected beams with the TM polarized mode of the Si waveguide, for light having a wavelength $\lambda=1550$ nm at an angle of incidence $\theta=45°$. In the grating spaces, the $SiO_2$ was completely removed to expose the Si waveguide surface. As such, the manufacturing method is greatly simplified by simply choosing an etch that does not dissolve the Si waveguide, but does remove the $SiO_2$. As the Si waveguide is of constant thickness, and as the $SiO_2$ layer prior to patterning and etching was of uniform height, a highly regular waveguide is produced in a cost effective manner.

The sensor surface was then functionalized, taking advantage of the native oxide layer of the Si waveguide. A cleaned surface was silanized with 3-aminopropylmethyl-diethoxysiloxane (APMDES) vapor and then rinsed with ethanol and dried. Next, the surface was biotinylated in a solution of N-hydroxysuccinimide (NHS) activated biotin in dimethylformamide (DMF) followed by rinsing with DMF and ethanol. Subsequently target binding of streptavidin molecules to the Biotin moities was performed. The sensor surface was dipped into a solution of streptavidin molecules dissolved in phosphate buffered saline (PBS) solution, and allowed to sit until substantially all of the biotin receptors are bound to respective target molecules. Throughout the target binding the temperature and pressure were ambient.

The sensor surface was dried before each optical spectrum was measured, and measurements were carried out in air. The experiments were carried out using P-polarized light from a tunable laser incident on the back of the wafer at $\theta=45°$. The molecular sensor is illuminated from the backside of the wafer. The reflected beam was collected and monitored by a photodetector as the incident wavelength was scanned.

Figure 7:
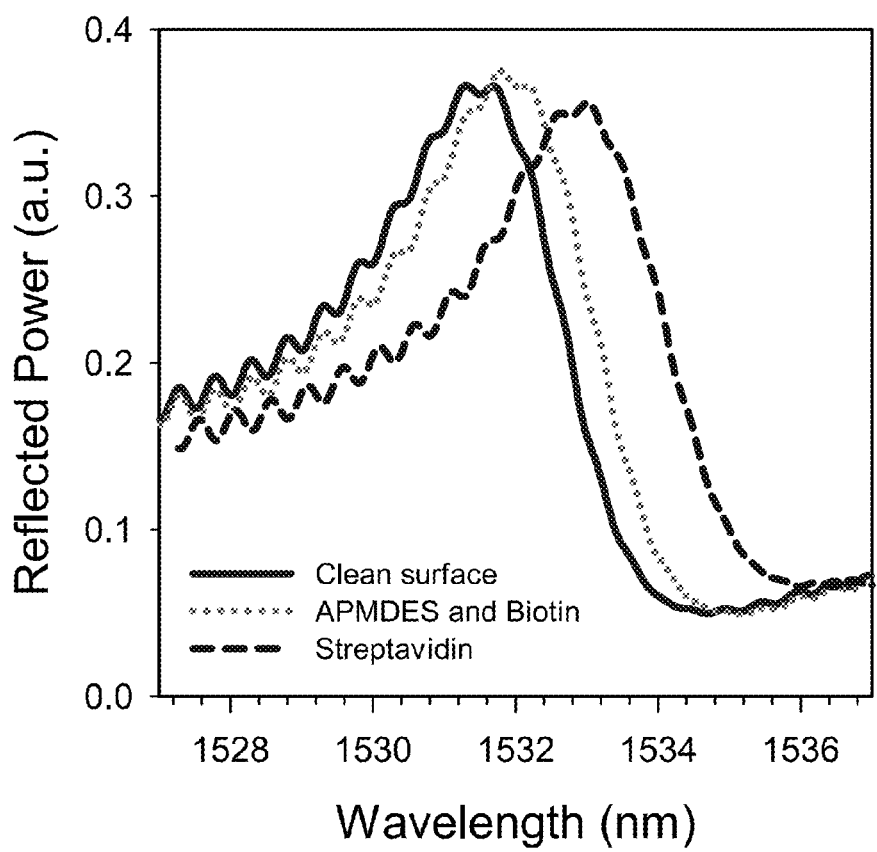
FIG. 7 is a graph of the measured specular reflected power as a function of wavelength for different evanescent field interactions.

FIG. 7 shows measured wavelength reflection response spectra for the clean sensor, after the sensor surface was functionalized, and finally after the sensor grating was exposed to a solution containing streptavidin molecules. The biotinylation functionalization produced a wavelength red shift of $\Delta\lambda_f$ of about 0.5 nm, and the subsequent streptavidin monolayer formation produced a further shift $\Delta\lambda_m$ about 1.0 nm. This shows a substantial change at least two orders of magnitude higher than is necessary to reliably discern the change.

The streptavidin monolayer has an estimated surface mass density near 1.6 $ng/mm^2$ [2], so the grating sensor response is about 1.6 $pg/mm^2/pm$. In our current bench top system, the resonance line peak is measured to within an accuracy of about ±1 pm giving a surface mass density resolution of about 3 $pg/mm^2$. This compares favourably to commercial SPR instruments. However the achieved level of detection (LOD) depends on the spectral line shape.

Figure 8:
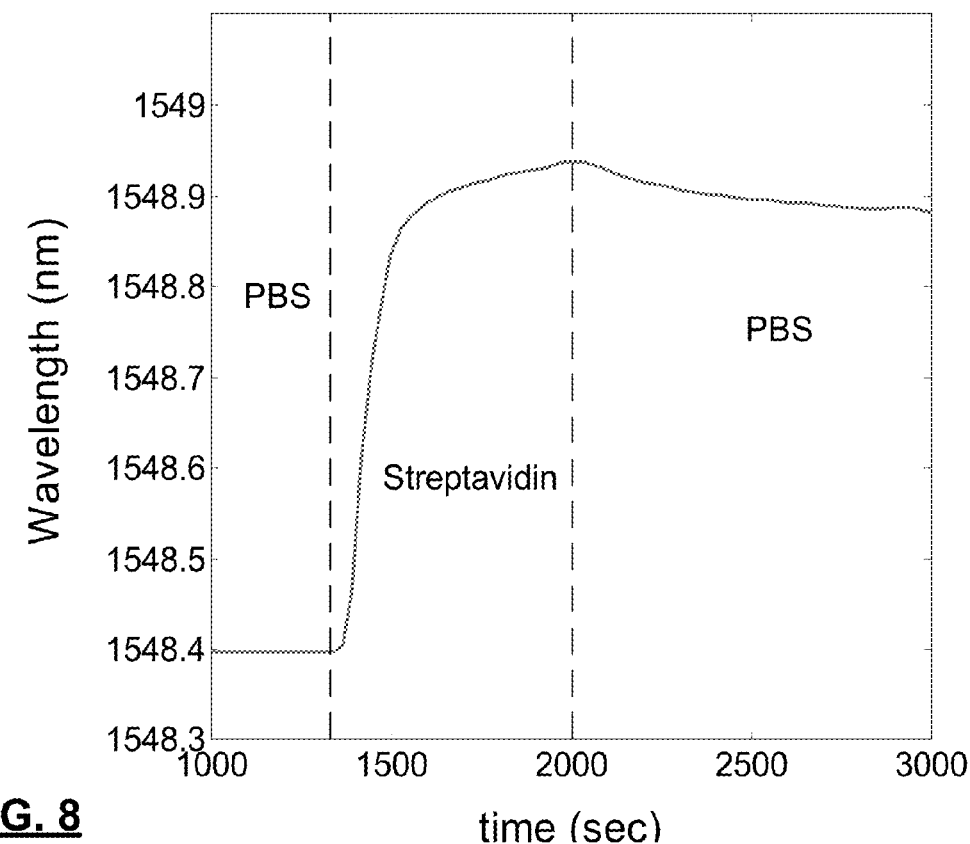
FIG. 8 is a graph of Streptavidin binding in PBS showing spectra taken continuously over a 3000 s period.

FIG. 8 illustrates a time-lapsed variation of peak wavelength for a continuously sampled spectral output during an experiment having three segments. In a first segment (from beginning until about 1300 s) the SOI detector was exposed to PBS. During the second segment, (~1300 to ~2000 s) Streptavidin is introduced into the buffer. It is noted that during the second segment there is a very rapid increase in the spectral peak from 1548.4 to 1548.85, followed by a leveling off caused by saturation of the binding of the Streptavidin to the functionalized surface, although there is a continuous rise in the spectral peak until the third segment of the test begins. During the third segment PBS is used to flush any free Streptavidin. While some loss in binding is observed over an extended period of time, the stability is generally satisfactory.

The grating structure used in this experiment can be further optimized to give much sharper resonances by using a thinner oxide layer, as demonstrated in FIG. 6. Since the binding induced resonance wavelength shift is independent of details of the grating, a sharper resonance leads to an immediate improvement to the sensitivity of the detector. Therefore this technology should be able to surpass the mass density resolution of SPR, where the resonance line width is ultimately limited by the extremely short propagation length of the plasmon at a metal surface.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

References, the entire contents of which are incorporated herein by reference:

[1] W. Lukosz, "Principles and sensitivities of integrated optical and surface plasmon sensors for direct affinity sensing and immunosensing," Biosensors and Bioelectronics, 6, 215-225 (1991).

[2] A. Densmore, D.-X. Xu, P. Waldron, S. Janz, P. Cheben, J. Lapointe, A. Delâge, B. Lamontagne, J. H. Schmid and E. Post, "A silicon on insulator photonic wire based evanescent field sensor," IEEE Photon. Technol. Lett. 18, 2520-2522 (2006).

[3] A. Densmore, D. X. Xu, P. Waldron, S. Janz, A. Delâge, J. Lapointe, P. Cheben, "Thin silicon waveguides for biological and chemical sensing," in *Proceedings of the SPIE, Vol. 6477*, (Bellingham, Wash., 2007), paper 43, pp. 6477181-64771810.

What is claimed is:

1. A molecular sensor comprising:
   a silicon on insulator (SOI) wafer comprising a single crystal silicon layer waveguide over a $SiO_2$ insulator layer, the waveguide having a diffraction grating on a sensor surface which is functionalized with receptors for a specific target molecule; such that the grating couples a polarized beam of light incident the sensor surface to excite a single mode in the waveguide and equally couples the single mode from the waveguide to form a sensed output signal; and the waveguide has a thickness of 10-400 nm, selected so that an overlap integral of the waveguide's mode intensity over the functionalized sensor surface is greater than 50% of the overlap integral over any other region of the same thickness within the waveguide.

2. The molecular sensor of claim 1 wherein the single mode has a peak evanescent field strength in the region of the sensor surface that is higher than the field strength at any point within the waveguide.

3. The molecular sensor of claim 1 wherein the thickness of the waveguide provides the single mode having a region of highest field strength within a distance from the sensor surface that corresponds to where a monolayer of the target molecules would be located.

4. The molecular sensor of claim 1 wherein the diffraction grating on the sensor surface is of a different composition than the silicon.

5. The molecular sensor of claim 1 wherein the diffraction grating on the sensor surface is substantially composed of a transparent polymer or inorganic compound.

6. The molecular sensor of claim 1 wherein the diffraction grating on the sensor surface is composed of silicon dioxide, or silicon nitride.

7. The molecular sensor of claim 1 wherein the diffraction grating on the sensor surface is a dielectric layer between 1 to 2000 nm thick, having a regular spacing matching a resonant wavelength of the single mode.

8. The molecular sensor of claim 1 wherein the diffraction grating on the sensor surface is formed by patterning the functionaiization of the sensor surface, by selective deposition of the receptors directly on the silicon waveguide surface.

9. The molecular sensor of claim 1 wherein the beam is incident the sensor surface from a bottom silicon layer of the SOI wafer.

10. The molecular sensor of claim 9 wherein the bottom insulator layer of the SOI is coated with an antireflection film.

11. The molecular sensor of claim 1 wherein the beam is P-polarized, and the single waveguide mode is a transverse magnetic (TM) mode.

12. The molecular sensor of claim 1 further comprising a detector for determining interference of a through-transmission beam or a compound specular reflection beam with the sensed output.

13. The molecular sensor of claim 1 further comprising a detector for detecting specular reflection power at a narrow wavelength band to effectively determine a shift in reflected or transmitted power of the beam that depends on the evanescent field interaction with the target molecules.

14. The molecular sensor of claim 1 further comprising a detector array for measuring a change in intensity of a diffracted ray of light.

15. The molecular sensor of claim 1 wherein the beam has a center wavelength of 1200 to 4000 nm, more preferably 1200-2000 nm, or one of 1280-1350 and 1480-1600 nm.

16. The molecular sensor of claim 1 wherein the waveguide is part of a silicon waveguide layer that extends beyond the grating, further comprising an array of like molecular sensors with similar or dissimilar functionalization.

17. A method of sensing a target molecule if present, within a fluid flow, the method comprising:
    providing a silicon on insulator (SOI) wafer comprising a single crystal silicon layer waveguide over a $SiO_2$ insulator layer, the waveguide having a diffraction grating on a sensor surface that is functionalized with receptors for a specific target molecule;
    applying the fluid flow to the sensor surface so that if the target molecule is present, it will preferentially attach to the receptors;
    applying a polarized beam of light incident the sensor surface so that the diffraction grating couples the beam to excite a single mode in the waveguide and equally couples the single mode from the waveguide to form a sensed output signal, the waveguide having a thickness of 10-400 nm, selected so that art overlap integral of the waveguide's mode intensity over the functionalized sensor surface is greater than 50% of the overlap integral over any other region of the same thickness within the waveguide; and
    determining a property of the sensed output that varies with interaction of the evanescent field with the target molecules if present.

18. The method of claim 17 wherein providing the SOI wafer comprises providing the diffraction grating on the sensor surface formed by patterning the functionalization of the top sensor surface, by selective deposition of the receptors directly on the silicon waveguide surface.

19. The method of claim 17 wherein applying the beam comprises directing an incident beam onto the sensor surface from a bottom silicon layer of the SOI.

20. The method of claim 17 wherein applying the beam comprises applying P-polarized beam to selectively couple with the single mode, which is a transverse magnetic (TM) mode.

21. The method of claim 17 wherein the thickness of the waveguide provided ensures that the single mode has a region of highest field strength within a distance from the sensor surface that corresponds to where a monolayer of the target molecules would be located.

22. The method of claim 17 wherein determining the property comprises interfering the sensed output beam with a transmitted beam or specular reflection.

23. The method of claim 17 wherein determining the property comprises detecting a change in the power of a higher order diffraction of the beam, or computing a measure that varies therewith.

* * * * *